United States Patent
Steinmann

Patent Number: 6,001,905
Date of Patent: Dec. 14, 1999

[54] POLYALKYLENE GLYCOL GROUP-CONTAINING HINDERED AMINES

[75] Inventor: Alfred Steinmann, Praroman, Switzerland

[73] Assignee: Ciba Specialty Chemicals Corporation, Tarrytown, N.Y.

[21] Appl. No.: 09/063,159

[22] Filed: Apr. 20, 1998

[30] Foreign Application Priority Data

Apr. 23, 1997 [CH] Switzerland ............... 951/97

[51] Int. Cl.⁶ ............... C08K 5/34; C07D 211/46
[52] U.S. Cl. ............... 524/99; 252/403; 524/100; 524/102; 544/231; 546/188; 546/190; 546/242; 546/247; 546/248
[58] Field of Search ............... 544/231; 252/403; 524/100, 102, 99; 546/188, 190, 242, 247, 248

[56] References Cited

U.S. PATENT DOCUMENTS

| | | | |
|---|---|---|---|
| 4,191,682 | 3/1980 | Ramey et al. | 546/5 |
| 4,526,972 | 7/1985 | Speranza et al. | 546/191 |
| 5,210,195 | 5/1993 | Lin et al. | 546/190 |

FOREIGN PATENT DOCUMENTS 0518807  4/1992  European Pat. Off.

*Primary Examiner*—Kriellion Sanders
*Attorney, Agent, or Firm*—Luther A.R. Hall; Kevin T. Mansfield

[57] ABSTRACT

A description is given of compounds of formula 1

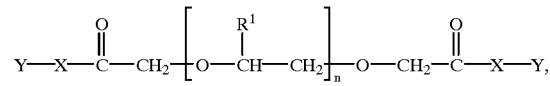

(1)

and of compounds of formula 2

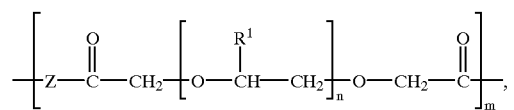

(2)

wherein X, Y and Z and the radicals $R^1$ and also m and n have the meanings claimed in claim 1.

The cited compounds are advantageously used e.g. for stabilizing organic material against the damaging effect of light, oxygen and/or heat.

18 Claims, No Drawings

POLYALKYLENE GLYCOL GROUP-CONTAINING HINDERED AMINES

The present invention relates to novel water-soluble polymeric HALS compounds, which can be obtained by reacting hindered amines [HALS], comprising functional groups, with polyalkylene glycol derivatives, to their use for stabilising organic materials against the damaging effect of light, oxygen and/or heat as well as to the corresponding stabilised compositions.

Polyoxyalklyenes containing terminal 2,2,6,6-tetramethyl-4-aminopiperidinyl radicals are known from U.S. Pat. No. 5,210,195 and are suggested as photostabilisers in photosensitive materials.

There is still a need for novel stabilisers of the bis(2,2,6,6-tetraalkyl-4-aminopiperidinyl)polyoxyalkylene type having improved performance properties, in particular good thermal stability and good solubility in water or aqueous solutions or generally in polar media, such as polyamides, polyethers, polyurethanes and the like.

It has now been found that certain compounds, starting from polyalkylene glycol derivatives and 2,2,6,6-tetramethylpiperidines, are surprisingly well suitable as stabilisers for, in particular, polar organic material. These compounds also have high temperature stability and thus permit higher processing temperatures in application and therefore a higher throughput when the products so stabilised are further processed.

Accordingly, this invention relates to compounds of formula 1

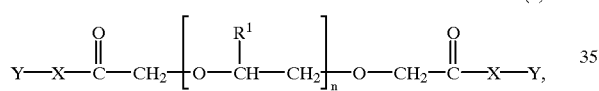
(1)

and compounds of formula 2

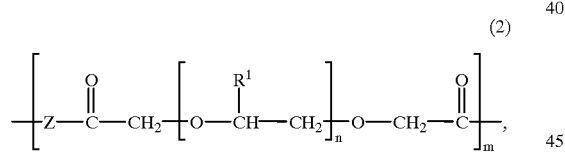
(2)

wherein $R^1$ is H or $CH_3$, and

Y is the group

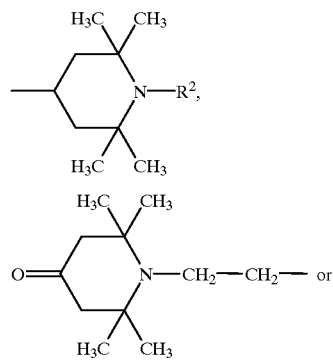

or

X is O or $NR^3$ $R^2$ is H, $C_1$–$C_{20}$alkyl, $C_1$–$C_{20}$hydroxyalkyl, O—$C_1$–$C_{20}$alkyl, CO—$C_1$–$C_{20}$alkyl, O—$C_5$–$C_8$cycloalkyl, $C_2$–$C_{20}$alkenyl, $C_2$–$C_{20}$alkynyl, $C_6$–$C_{20}$aryl, CO—$C_6$–$C_{20}$aryl, $C_7$–$C_{20}$aralkyl, CO—$C_7$–$C_{20}$aralkyl, and $R^3$ is H, $C_1$–$C_{20}$alkyl or

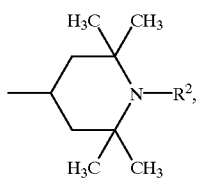

and $R^4$ is H, $C_1$–$C_{20}$alkyl, CO—$C_1$–$C_{20}$alkyl, CO—$C_6$–$C_{20}$aryl or CO—$C_7$–$C_{20}$aralkyl, and Z is

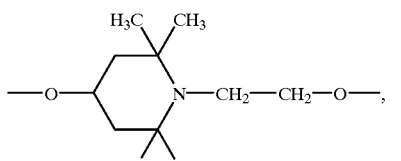

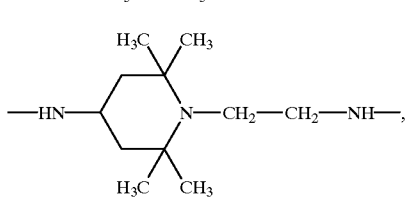

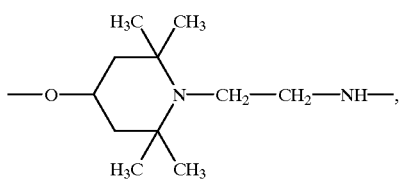

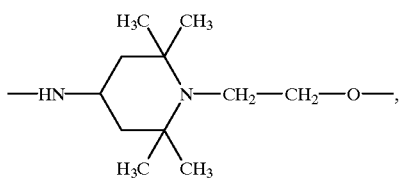

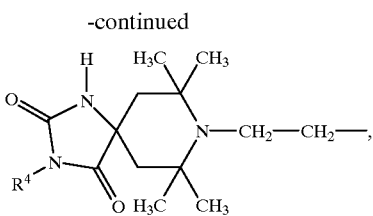

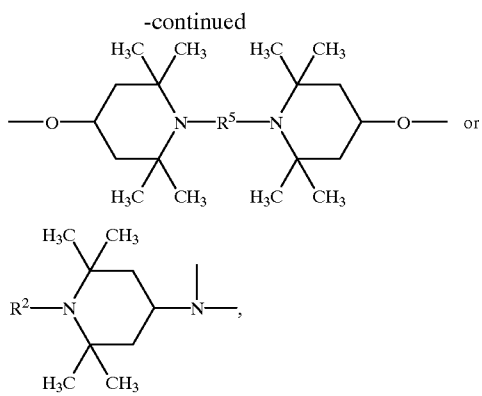

and

R$^5$ is C$_1$–C$_{20}$alkylene, C$_2$–C$_{20}$alkenylene or C$_2$–C$_{20}$alkynylene, and n is a number from 1 to 100, and m is a number from 1 to 100.

R$^2$, R$^3$ and R$^4$ defined as C$_1$–C$_{20}$ alkyl can be straight-chain or branched and are, for example, methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylandecyl, dodecyl, 1,1,3,3,5,5-hexamethylhexyl, etc.

The alkyl groups R$^2$, R$^3$ and R$^4$ preferably contain 1 to 12 carbon atoms, R$^2$ and R$^4$ preferably contain 1 to 8 carbon atoms.

In the case of R$^2$ defined as C$_1$–C$_{20}$hydroxyalkyl the straight-chain or branched alkyl chain contains 1 to 20 carbon atoms and the OH-group(s) can be at any possible position of said chain(s).

The radical preferably contains 1 to 3, particularly preferably 1 or 2, hydroxyl groups, such as hydroxymethyl, hydroxyethyl, 3-hydroxypropyl, 2-hydroxypropyl, 4-hydroxybutyl, 3-hydroxybutyl, 2-hydroxybutyl, 5-hydroxypentyl, 4-hydroxypentyl, 3-hydroxypentyl, 2-hydroxypentyl, 6-hydroxyhexyl, 5-hydroxyhexyl, 4-hydroxyhexyl, 3-hydroxyhexyl, 2-hydroxyhexyl, 7-hydroxyheptyl, 6-hydroxyheptyl, 5-hydroxyheptyl, 4-hydroxyheptyl, 3-hydroxyheptyl, 2-hydroxyheptyl, 8-hydroxyoctyl, 7-hydroxyoctyl, 6-hydroxyoctyl, 5-hydroxyoctyl, 4-hydroxyoctyl, 3-hydroxyoctyl, 2-hydroxyoctyl, 9-hydroxynonyl, 10-hydroxydecyl, 11-hydroxyandecyl, 12-hydroxydodecyl, 13-hydroxytridecyl, 14-hydroxytetradecyl, 15-hydroxypentadecyl, 16-hydroxyhexadecyl, 17-hydroxyheptadecyl, 18-hydroxyoctadecyl or 20-hydroxyeicosyl.

R$^2$ defined as C$_5$–C$_8$cycloalkyl is cyclopentyl, cyclohexyl, cycloheptyl and cyclooctyl.

Cyclohexyl is preferred.

R$^2$ defined as C$_2$–C$_{20}$ alkenyl is typically vinyl, 1-propenyl, 2-propenyl, 1-butenyl, 2-butenyl, 3-butenyl, etc. Alkenyl groups containing 2 to 12, in particular 2 to 8, carbon atoms are preferred.

R$^1$ defined as C$_2$–C$_{20}$alkynyl is, for example, ethynyl, 1-propynyl, 2-propynyl, 1-butynyl, 2-butynyl, 3-butynyl, etc. Such alkynyl groups preferably contain 2 to 12 carbon atoms, particularly preferably 2 to 8 carbon atoms.

R$^2$ and R$^4$ defined as C$_6$–C$_{20}$aryl are typically phenyl, naphthyl, anthracenyl, phenanthrenyl.

Phenyl is preferred.

R$^2$ and R$^4$ defined as aralkyl are, for example, benzyl, phenethyl, 3-phenylpropyl, α-methylbenzyl or α,α'-dimethylbenzyl.

Benzyl is preferred.

R$^5$ defined as C$_1$–C$_{20}$alkylene is a branched or unbranched radical, such as methylene, ethylene, propylene, trimethylene, tetramethylene, pentamethylene, hexamethylene, heptamethylene, octamethylene, decamethylene, dodecamethylene or octadecamethylene. C$_1$–C$_{12}$Alkylene is preferred and C$_1$–C$_8$alkylene is particularly preferred.

R$^5$ defined as C$_2$–C$_{20}$alkenylene is typically vinylene, methylvinylene, octenylethylene or dodecenylethylene. C$_2$–C$_{12}$Alkenylene is preferred and C$_2$–C$_8$alkenylene is particularly preferred.

R$^5$ in the definition of C$_2$–C$_{20}$alkynylene is, for example, ethynylene, propynylene, 1-butynylene, 2-butynylene, 1-pentynylene, 2-pentynylene, 1-hexynylene, 2-hexynylene, 3-hexynylene, etc. C$_2$–C$_{12}$Alkynylene is preferred and C$_2$–C$_8$alkynylene is particularly preferred.

Preferred compounds of formulae 1 and 2 are those, wherein R$^1$ is hydrogen.

Other preferred compounds of formulae 1 and 2 are those, wherein

R$^2$ is H, C$_1$–C$_{12}$alkyl, C$_1$–C$_{12}$hydroxyalkyl, O—C$_1$–C$_{12}$alkyl, CO—C$_1$–C$_{12}$alkyl, O—C$_5$–C$_8$cycloalkyl, C$_2$–C$_{12}$alkenyl, C$_2$–C$_{12}$alkynyl, C$_6$–C$_{14}$aryl, CO—C$_6$–C$_{14}$aryl, C$_7$–C$_{15}$aralkyl or CO—C$_7$–C$_{15}$aralkyl.

Particularly preferred compounds are those of formulae 1 and 2, wherein

R$^2$ is H, C$_1$–C$_8$alkyl, O—C$_1$–C$_8$alkyl, O—C$_5$–C$_8$cycloalkyl, C$_2$–C$_8$alkenyl or C$_2$–C$_8$alkynyl.

Other preferred compounds of formula 1 are those, wherein

R$^3$ is H, C$_1$–C$_{12}$alkyl or

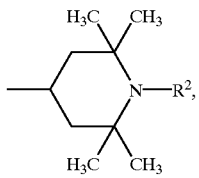

and

R$^4$ is H, C$_1$–C$_{12}$alkyl, CO—C$_1$–C$_{12}$alkyl, CO—C$_6$–C$_{14}$aryl or CO—C$_7$–C$_{15}$aralkyl.

Very particularly preferred compounds are those of formula 1, wherein

R$^3$ is H or

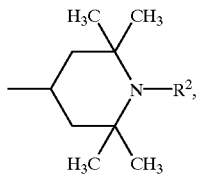

and

R$^4$ is H, C$_1$–C$_8$alkyl, CO—C$_1$–C$_8$alkyl, CO-phenyl or CO-phenylalkyl.

Particularly preferred compounds are those of formula 2, wherein

Z is

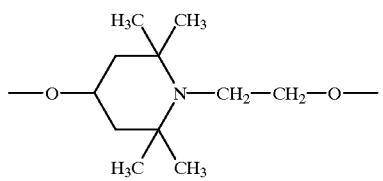

or

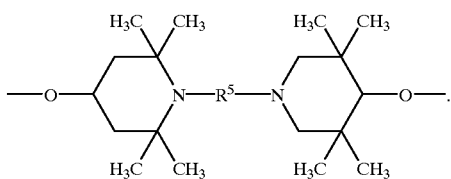

Preferred compounds of formula 1 and 2 are those, wherein n is a number from 1 to 50.

Other preferred compounds are those of formula 2, wherein m is a number from 1 to 50.

The compounds of formula 1 are preferred.

Particularly preferred compounds are those of formula 1, wherein

Y is a group

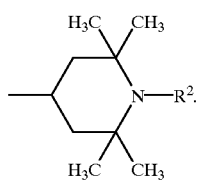

Very particularly preferred compounds are those of formula 1, wherein

Y is a group

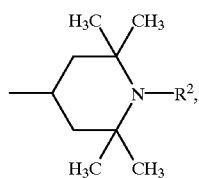

$R^2$ is H or $C_1$–$C_4$alkyl, $R^3$ is H or

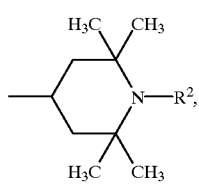

and n is a number from 5 to 25.

The novel compounds are prepared in a manner known per se, for example by reacting a polyalkylene glycol diacid of formula 3

(3)

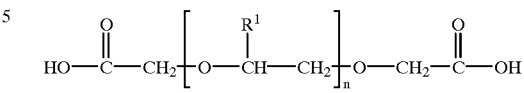

or a derivative thereof (e.g. halide, ester, anhydride) with, in particular, 2 molar equivalents of an amine or alcohol of formula Y—$NHR^3$ or Y—OH (for the preparation of compounds of formula 1) or, preferably, with one molar equivalent of a difunctional compound of formula H—Z—H (for the preparation of compounds of formula 2). The cited educts are either commercially available or can be easily prepared by known processes. In the case of a secondary amine, the amide is expediently prepared by reacting the corresponding polyalkylene glycol diacid chloride, which can be prepared from the polyalkylene glycol diacid and thionyl chloride in known manner, with the amine. It may also be very convenient to obtain the corresponding novel compounds by transesterification from the polyalkylene glycol acid dimethyl esters. Such transesterifications are commonly known.

The reactions are conveniently carried out in an inert solvent. The solvents used may be polar or unpolar organic solvents, for example hydrocarbons, halogenated hydrocarbons, esters, ethers, ketones, amides, nitrites, tert-amines or sulfoxides; suitable are e.g. toluene, hexane, cyclohexane, ligroin, petroleum ether and other hydrocarbon mixtures, dimethylformamide, tetrahydrofuran, dioxane, chloroform, diethyl ether, dimethyl sulfoxide and acetonitrile; particularly preferred are chloroform, tetrahydrofuran and toluene.

During the reaction the temperature can be in the range from −20 to 200° C., usefully in the range from 0 to 180° C., preferably in the range from 10 to 140° C.

For the duration of the reaction, the temperature of the reaction mixture can be kept in the boiling range (reflux). To this purpose, a reaction mixture containing a solvent is heated to the boiling point, in general under normal pressure, and the evaporated solvent is condensed by means of a suitable condenser and is then returned to the reaction mixture.

The reactions can be carried out with the exclusion of oxygen, for example by flushing with an inert gas such as argon. However, oxygen does not interfere in every case so that the reaction can also be carried out without taking the above measures.

After the reaction is complete, working up can be carried out by customary methods. The mixture is conveniently first diluted with water, for example by adding the reaction mixture to 1–4 times the volume of (ice-)water, and the product can then be isolated direct or may be extracted. Chloroform, ethyl acetate or toluene are suitable for the extraction. If extraction is carried out, then the product can be isolated in customary manner by removing the solvent, which is conveniently done after drying the organic phase. It is also possible to use additional purification steps, for example washing with aqueous sodium hydrogencarbonate solution, dispersing activated charcoal, chromatographing over silica gel, filtering, recrystallising and/or distilling.

The compounds of this invention are particularly suitable for stabilising organic materials against thermal, oxidative and actinic degradation.

Typical examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (VLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile nitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α, β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from polyepoxides, for example from bis glycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

This invention therefore also relates to compositions, which comprise a) an organic material susceptible to oxidative, thermal or/and actinic degradation/build-up, and b) at least one novel compound according to claim 1, as well as to the use of the novel compounds for stabilising organic material against oxidative, thermal or actinic degradation/build-up.

This invention also encompasses a process for stabilising organic material against thermal, oxidative or/and actinic degradation/build-up, which comprises adding to this material at least one novel compound.

Particularly interesting is the use of the novel compounds as stabilisers in synthetic organic polymers as well as corresponding compositions.

The organic materials to be protected are preferably natural, semi-synthetic or, especially, synthetic organic materials. Particularly preferred are synthetic organic polymers or mixtures of such polymers, in particular thermoplastic polymers such as polyesters and polyamides. Other particularly preferred organic materials are surface coating compositions. Surface coating compositions which are advantageously to be stabilised according to this invention are described, inter alia, in Ullmann's Encyclopedia of Industrial Chemistry, 5. Ed., Vol. A 18, pages 359–464, VCH Verlagsgesellschaft, Weinheim 1991.

Particularly interesting is the use of the novel compounds as stabilisers for surface coatings, e.g. for lacquers. In another of its aspects, this invention thus relates to compositions wherein component A is a film-forming binder.

The inventive surface coating contains per 100 parts by weight of solid binder A preferably 0.01–10 parts by weight, more preferably 0.05–10 parts by weight, most preferably 0.1–5 parts by weight, of the novel stabiliser B.

Multicoat systems are also possible here, in which case the concentration of component B in the top coat can be higher, for example from 1 to 15 parts by weight, preferably from 3 to 10 parts by weight, of component B per 100 parts by weight of solid binder A.

The use of the novel compounds as stabilisers in coatings has the additional advantage of preventing delamination, i.e. the peeling off of the coating from the substrate. This advantage is especially important in the case of metallic substrates and also in multicoat systems on metallic substrates.

Suitable binders (component A) are, in principle, all those customary in the art, for example those described in Ullmann's Encyclopedia of Industrial Chemistry, 5. Ed., Vol. A 18, pages 368–426, VCH Verlagsgesellschaft, Weinheim 1991. In general, the binder is a film-forming binder based on a thermoplastic or heat-curable resin, preferably on a heat-curable resin. Typical examples are alkyd, acrylic, polyester, phenolic, melamine, epoxy and polyurethane resins and their mixtures.

Component A can be a binder which can be cured cold or hot, and the addition of a curing catalyst may be advantageous. Suitable catalysts which accelerate the curing of the binder are described, inter alia, in Ullmann's Encyclopedia of Industrial Chemistry, Vol. A 18, p. 469, VCH Verlagsgesellschaft, Weinheim 1991.

Preferred surface coatings are those, wherein component A is a binder consisting of a functional acrylate resin and a crosslinker.

Illustrative examples of surface coatings with special binders are:

1. Lacquers based on cold- or heat-crosslinkable alkyd, acrylate, polyester, epoxy or melamine resins or on mixtures of such resins, if required with addition of a curing catalyst;

2. two-component polyurethane lacquers based on hydroxyl group-containing acrylate, polyester or polyether resins and aliphatic or aromatic isocyanates, isocyanurates or polyisocyanates;

3. one-component polyurethane lacquers based on blocked isocyanates, isocyanurates or polyisocyanates which are unblocked during stoving;

4. one-component polyurethane lacquers based on aliphatic or aromatic urethanes or polyurethanes and hydroxyl group-containing acrylate, polyester or polyether resins;

5. one-component polyurethane lacquers based on aliphatic or aromatic urethanes or polyurethanes containing free amine groups in the urethane structure and melamine resins or polyether resins, with or without the addition of a curing catalyst;

6. two-component lacquers based on (poly)ketimines and aliphatic or aromatic isocyanates, isocyanurates or polyisocyanates;

7. two-component lacquers based on (poly)ketimines and on an unsaturated acrylate resin or polyacetoacetate resin or methacrylamidoglycolate methyl ester;

8. two-component lacquers based on carboxyl- or amino group-containing polyacrylates and polyepoxides;

9. two-component lacquers based on anhydride group-containing acrylate resins and on a polyhydroxy or polyamino component;

10. two-component lacquers based on acrylate-containing anhydrides and polyepoxides;

11. two-component lacquers based on (poly)oxazolines and anhydride group-containing acrylate resins or unsaturated acrylate resins or aliphatic or aromatic isocyanates, isocyanurates or polyisocyanates;

12. two-component lacquers based on unsaturated polyacrylates and polymalonates;

13. thermoplastic polyacrylate lacquers based on thermoplastic acrylate resins or externally crosslinking acrylate resins in combination with etherified melamine resins;

14. paint systems based on siloxane-modifled or fluorine-modified acrylate resins.

In addition to components A and B, the novel surface coating preferably comprises as component C at least one additional light stabiliser, in particular a UV absorber, for example from the groups 2.1–2.4, 2.7 or 2.8 of the costabiliser list given hereinafter. The addition of 2-hydroxyphenyl-2H-benztriazoles and/or 2-hydroxyphenyl-1,3,5-triazines is of particular technical interest.

The additional light stabiliser (component C) is preferably used in an amount of 0.05–5 parts by weight per 100 parts by weight of the solid binder.

In addition to components A, B and, optionally, C, the surface coating can comprise other components, for example solvents, pigmente, colourants, plasticisers, stabilisers, thixotropic agents, drying catalysts and/or flow control agents.

Possible components are, for example, those described in Ullmann's Encyclopedia of Industrial Chemistry, 5. Ed., Vol. A 18, pages 429–471, VCH Verlagsgesellschaft, Weinheim 1991.

Possible drying or curing catalysts are typically organic metal compounds, amines, amino group-containing resins or/and phosphines. Organic metal compounds are, for example, metal carboxylates, in particular those of the metals Pb, Mn, Co, Zn, Zr or Cu, or metal chelates, in particular those of the metals Al, Ti or Zr, or organometallic compounds such as organotin compounds.

Illustrative examples of metal carboxylates are the stearates of Pb, Mn or Zn, the octoates of Co, Zn or Cu, the naphthenates of Mn and Co or the corresponding linoleates, resinates or tallates.

Typical examples of metal chelates are the aluminium, titanium or zirconium chelates of acetylacetone, ethylacetyl acetate, salicylaldehyde, salicylaldoxime, o-hydroxyacetophenone or ethyltrifluoroacetyl acetate and the alkoxides of these metals.

Typical examples of organotin compounds are dibutyltin oxide, dibutyltin dilaurate or dibutyltin dioctoate.

Illustrative examples of amines are, in particular, tertiary amines, such as tributylamine, triethanolamine, N-methyldiethanolamine, N-dimethylethanolamine, N-ethylmorpholine, N-methylmorpholine or diazabicyclooctane (triethylenediamine) and their salts. Other examples are quaternary ammonium salts, such as trimethylbenzylammonium chloride.

Amino group-containing resins are at the same time binders and curing catalysts. Typical examples thereof are amino group-containing acrylate copolymers.

The curing catalysts may also be phosphines, for example triphenylphosphine.

The surface coatings of this invention can also be radiation-curable. In this case the binder consists essentially of monomeric or oligomeric compounds having ethylenically unsaturated bonds (prepolymers) which are cured by actinic radiation after their application, i.e they are converted to a crosslinked high molecular weight form. A UV-curing system usually additionally comprises a photoinitiator. Corresponding systems are described in the above-mentioned publication, Ullmann's Encyclopedia of Industrial Chemistry, 5. Ed., Vol. A 18, pages 451–453. In radiation-curable surface coatings the novel stabilisers can also be used without addition of sterically hindered amines.

The novel surface coatings can be applied to any substrate, for example to metal, wood, plastic or ceramic materials. They are preferably used as a top coat for painting automotives. If the top coat consists of two layers, the lower layer being pigmented and the upper layer being unpigmented, then the novel surface coating can be used for the upper or lower layer or for both layers, but preferably for the upper layer.

The novel surface coatings can be applied to the substrates by the customary methods, for example by coating, spraying, flow coating, immersion or electrophoresis; see also Ullmann's Encyclopedia of Industrial Chemistry, 5. Ed., Vol. A 18, pages 491–500.

Depending on the binder system, the surface coatings can be cured at room temperature or by heating. The coatings are preferably cured at 50–150° C., powder coatings also at higher temperatures.

The surface coatings obtained according to this invention have excellent stability against the damaging effects of light, oxygen and heat. Particular mention is to be made of the good stability to light and weathering of the surface coatings so obtained, for example lacquers.

Accordingly, this invention also relates to a surface coating, in particular a lacquer, which is stabilised by addition of at least one compound against the damaging effects of light, oxygen and heat. This lacquer is preferably a top coat for automotives. This invention also relates to a process for stabilising a surface coating based on organic polymers against damage by light, oxygen and/or heat, which comprises admixing at least one novel compound to the surface coating, as well as to the use of the novel compounds in surface coatings as stabilisers against damage by light, oxygen and/or heat.

The surface coatings can contain an organic solvent or solvent mixture in which the binder is soluble. However, the surface coating can also be an aqueous solution or dispersion. The vehicle may also be a mixture of an organic solvent and water. The surface coating may also be a high solids lacquer or may be solvent-free (e.g. powder coating). Powder coatings are, for example, those described in Ullmann's Encyclopedia of Industrial Chemistry, 5. Ed., A 18, pages 438–444. The powder coating can also be obtained in the form of a powder slurry, i.e. of a dispersion of the powder preferably in water.

The pigments can be inorganic, organic or metallic pigments. The novel surface coatings preferably do not contain any pigments and are used as clear varnish formulations.

It is also preferred to use the surface coatings as finishing lacquer for applications in the automotive industry, in particular as pigmented or unpigmented lacquer top coat. However, it is also possible to use the surface coating for the coats underneath.

Other materials to be stabilised with the novel compounds are photographic materials. These will be understood as being in particular those which are described in Research Disclosure 1990, 31429 (pages 474–480) for photographic reproduction and other reproduction technologies.

The novel compounds are generally added to the material to be stabilised in amounts of 0.01 to 10%, preferably of 0.01 to 5%, more preferably of 0.01 to 2%, based on the total weight of the composition to be stabilised. The novel compounds are particularly preferably used in amounts of 0.05 to 1.5%, most preferably of 0.1 to 0.5%.

The incorporation of the novel compounds and further optional additives into the materials can be carried out by conventional technological methods, typically by admixture or by application. In the case of polymers, in particular of synthetic polymers, the incorporation can be carried out before or after shaping or also by applying the dissolved or dispersed compound to the polymers, if necessary with subsequent evaporation of the solvent. Elastomers can also be stabilised as latices. The novel compounds can also be incorporated into polymers by being added before, during or immediately after the polymerisation of the corresponding monomers or before crosslinking. The novel compounds can be added as such or also in encapsulated form (e.g. in waxes, oils or polymers). Where the addition is carried out before or during the polymerisation, the novel compounds can also serve as regulators for the chain lengths of the polymers (chain terminators).

The novel compounds can also be added to the plastics to be stabilised in the form of a masterbatch comprising these compounds in a concentration of 2.5 to 25% by weight.

The incorporation of the novel compounds can conveniently be carried out by the following methods:

- as emulsion or dispersion (e.g. to latices or emulsion polymers),
- as dry mixture during the admixture of additional components or polymer mixtures,
- by direct addition to the processing apparatus (e.g. extruder, internal mixer and the like)
- as solution or melt.

The polymer compositions can be used in different form or processed to different products, typically films, fibres, tapes, mouldings, profiles, or binders for paints systems, adhesives or putties.

In addition to the novel compounds, the compositions of this invention can comprise as additional component (C) one or several customary additives, such as the following:

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)-disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl) pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, pane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyidiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyidiphenylamines, a mixture of mono- and dialkylated dodecyldiphenylamines, a mixture of mono- and dialkylated isopropyl/isohexyldiphenylamines, a mixture of mono- und dialkylated tert-butyidiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl) sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)

phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$]$_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl]-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, mate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3, 5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1, 2,3,4-butane-tetracarboxylate, 1,1'-(1,2-ethanediyl)-bis(3,3, 5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decan-2, 4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)-ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)-pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)-ethane and 2,4,6-trichloro-1,3,5-triazine as well as 4-butylamino-2,2,6, 6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3, 8-diaza-4-oxo-spiro[4,5]decane, a reaction product of 7,7,9 9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl) ethene, N,N'-bis-formyl-N,N'-bis(2,2,6,6-tetramethyl-4-piperidyl)hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyl-oxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy) phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1- oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butyl-phenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz-[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo [triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite.

Especially preferred are the following phosphites:

Tris(2,4-di-tert-butylphenyl) phosphite (Irgafos®168, Ciba-Geigy), tris(nonylphenyl) phosphite,

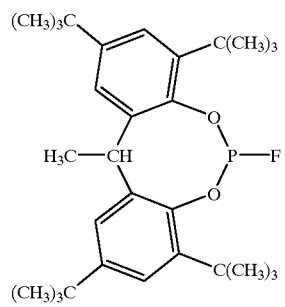
(A)

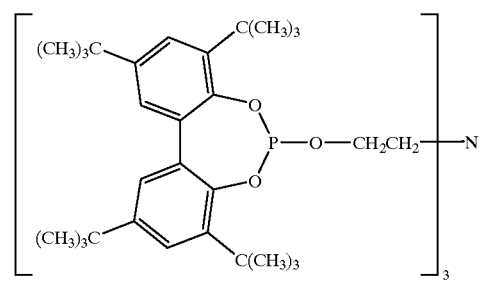
(B)

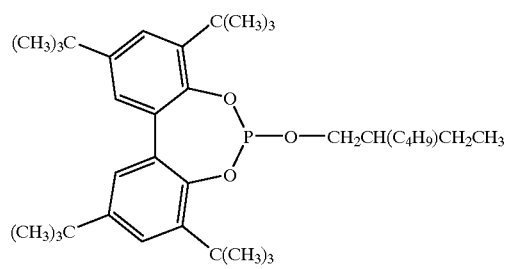
(C)

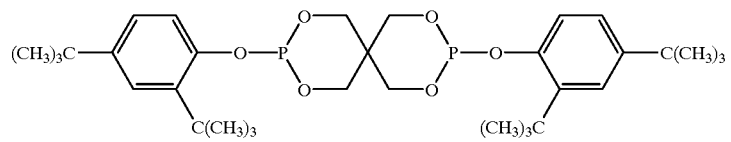
(D)

-continued (E)
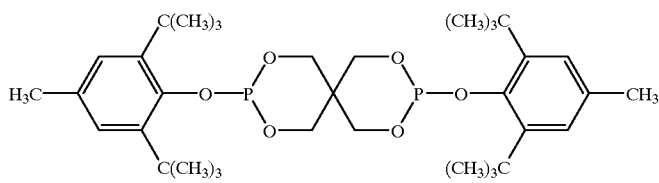

(F)

(G)
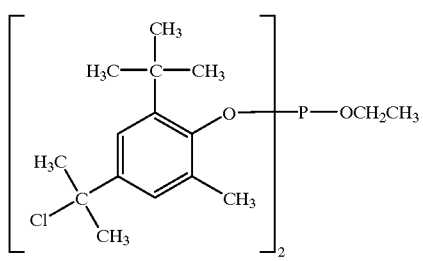

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, zinc stearate, magnesium behenate, magnesium stearate, sodium ricinoleate and potassium palmitate, antimony pyrocatecholate or zink pyrocatecholate.

11. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

These additional additives are conveniently used in amounts of 0.1–10, typically of 0.2–5% by weight, based on the polymer to be stabilised.

The invention is illustrated by the following Examples. In the Examples as well as in the remaining description and in the patent claims, parts or percentages are by weight, unless otherwise stated. The following abbreviations are used in the Examples:

ax: axial
$CDCl_3$: deuterochloroform
of th.: of theory eq: equatorial

¹H-NMR: nuclear magnetic resonance of the nuclide ¹H

MALDI-MS: matrix assisted laser desorption/ionisation-mass spectroscopy $M_n$: number average of the relative molar mass (unit g/mol)

$M_w$: mass average of the relative molar mass (unit g/mol)

PEG: polyethylene gylcol(600)

THF: tetrahydrofuran

Working Examples

EXAMPLE 1

PEG-diacid-bis(3,3,5,5-tetramethylpiperidinylamide)

60 g (0.1 mol) of PEG-diacid and 32 g (0.2 mol) of 4-amino-2,2,6,6-tetramethylpiperidine are heated to 180° C. under inert gas. The mixture is allowed to react for about 5 hours at this temperature, the water which forms during the reaction distilling over via a distillation head. The mixture is then cooled to room temperature and the reaction product is completely dissolved in chloroform. The organic phase is washed with a sodium chloride-saturated solution of sodium hydroxide. The organic phase is then dried with sodium sulfate and the solvent is removed in a rotary evaporator. Remaining residues of the solvent are then removed under high-vacuum at 90° C.

This gives 60 g (75% of th.) of a viscous liquid which is very highly soluble in water.

| Microanalysis: | calculated | found |
|---|---|---|
| C | 63.2% | 59.7% |
| H | 10.2% | 10.0% |
| N | 7.0% | 7.0% |

¹H-NMR (CDCl₃):
0.94–1.02 ppm (t) ax-CH₂ (piperidine ring)
1.14 and 1.26 ppm (s) CH₃ (piperidine ring)
1.85–1.90 ppm (2d) eq-CH₂ (piperidine ring)
3.63–3.70 ppm (m) —O—CH₂—CH₂—O—
3.96 ppm (s) —O—CH₂—CO—
4.26–4.31 ppm (m)

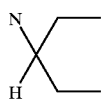

6.64 ppm (d) —NH—CO—
MALDI-MS: $M_n$=796 $M_w$=867

EXAMPLE 2

PEG-diacid-bis(3,3,4,5,5-pentamethylpiperidinylamide)

110 g (183 mmol) of PEG-diacid and 70 g (412 mmol) of 4-amino-1,2,2,6,6-pentamethylpiperidine are reacted as described in Example 1 and worked up.

This gives 105 g (58% of th.) of a viscous liquid which is highly soluble in water.

| Microanalysis: | calculated | found |
|---|---|---|
| C | 60.1% | 59.6% |
| H | 9.8% | 9.8% |
| N | 6.4% | 7.1% |

¹H-NMR (CDCl₃):
1.08 and 1.16 ppm (s) CH₃ (piperidine ring)
1.25–1.34 ppm (t) ax-CH₂ (piperidine ring)
1.76–1.81 ppm (2d) eq-CH₂ (piperidine ring)
2.24 ppm (s) CH₃—N
3.63–3.69 ppm (m) —O—CH₂—CH₂—O—
4.01 ppm (s) —O—CH₂—CO—
4.15–4.20 ppm (m)

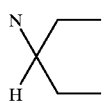

6.67 ppm (d) —NH—CO—
MALDI-MS: $M_n$=847 $M_w$=911

EXAMPLE 3

PEG-diacid-bis(3,3,4,5,5-pentamethylpiperidin-1-yl ester)

3a) PEG-diacid Dimethyl Ester

In a 1 liter round bottom flask, equipped with magnetic stirrer and reflux condenser, 300 g (0.5 mol) of PEG-diacid are dissolved under argon in 300 ml of methanol. After adding 10 ml of concentrated sulfuric acid, the solution is refluxed overnight. After cooling to room temperature, the solution is poured on ice. Extraction is then carried out with chloroform and the organic phase is washed with a sodium chloride-saturated solution of sodium hydroxide. The organic phase is dried and the solvent is completely removed. This gives 250 g (83% of th.) of a clear viscous liquid.

| Microanalysis: | calculated | found |
|---|---|---|
| C | 51.8% | 52.8% |
| H | 8.3% | 8.6% |

¹H-NMR (CDCl₃):
3.64–3.76 ppm (m, 40H) —O—CH₂—CH₂—O—
3.77 ppm (s, 6H) COOCH₃
4.23 ppm (s, 4H) —O—CH₂—CO—

3b) PEG-diacid-bis(3,3,4,5,5-pentamethylpiperidin-1-yl ester)

A 1 liter round bottom flask, equipped with magnetic stirrer and distillation head, is charged under argon with 120 g (0.2 mol) of the dimethyl ester prepared under 3a), 69 g (0.4 mol) of 4-hydroxy-1,2,2,6,6-pentamethylpiperidine, 7 g of dibutyltin oxide and 600 ml of xylene. After heating to 140° C., the solution is kept at this temperature until no methanol distills over anymore. Heating is then increased so that xylene also distills over slowly. After about 100 ml of xylene are removed by distillation, the mixture is cooled to room temperature and the residual solvent is then removed in a rotary evaporator. The residue is taken up in chloroform and the organic phase is washed with a sodium chloride-saturated solution of sodium hydroxide. The organic phase is dried, filtered and the solvent is removed in a rotary evaporator. This gives 100 g (60% of th.) of a viscous liquid.

| Microanalysis: | | |
|---|---|---|
| | calculated | found |
| C | 59.1% | 58.4% |
| H | 9.5% | 9.9% |
| N | 2.6% | 2.5% |

$^1$H-NMR (CDCl$_3$):
1.08 and 1.16 ppm (s) CH$_3$ (piperidine ring)
1.47–1.54 ppm (t) ax-CH$_2$ (piperidine ring)
1.83–1.89 ppm (2d) eq-CH$_2$ (piperidine ring)
2.24 ppm (s) CH$_3$—N
3.63–3.71 ppm (m) —O—CH$_2$—CH$_2$—O—
4.11 ppm (s) —O—CH$_2$—CO—
5.08–5.16 ppm (m)

MALDI-MS: M$_n$=955 M$_w$=1005

EXAMPLE 4

PEG-diacid-bis[di(3,3,4,5,5-pentamethylpiperidinyl) amide]

4a) PEG-diacid dichloride 90 g (0.15 mol) of anhydrous PEG-diacid are dissolved in 300 ml of chloroform and charged with 150 g of thionyl chloride. This solution is refluxed until no evolution of SO$_2$ can be detected anymore (after about 2 hours). The reaction solution is allowed to cool to room temperature and excess thionyl chloride and the solvent are then removed by evaporation in a rotary evaporator. The residue is then dried under high-vacuum at room temperature. This gives 98 g (100% of th.) of a liquid.

| Microanalysis: | | |
|---|---|---|
| | calculated | found |
| C | 47.63% | 48.03% |
| H | 7.33% | 7.12% |
| Cl | 10.84% | 11.22% |

4b) PEG-diacid-bis[di(3,3,4,5,5-pentamethylpiperidinyl) amide]

In a 750 ml sulfonation flask, equipped with KPG stirrer, dripping funnel and internal thermometer, 30 g (46 mmol) of the PEG-diacid dichloride prepared under 4a) are dissolved under argon in 150 ml of chloroform. A dripping funnel is charged with a solution consisting of 30 g (92 mmol) of di(3,3,4,5,5-pentamethylpiperidinyl)amine in 150 ml of chloroform. The amine is slowly added dropwise at ≦10° C.

The mixture is then allowed to react overnight. The clear solution is then poured on 20 ml of ice-cold 50-% sodium hydroxide solution and the organic phase is extracted by shaking. The organic phase is separated, dried with sodium sulfate and the solvent is then removed by evaporation. The residue is dried under high-vacuum at 50° C. This gives 102 g (90% of th.) of a viscous liquid.

| Microanalysis: | | |
|---|---|---|
| | calculated | found |
| C | 64.49% | 65.28% |
| H | 10.42% | 10.83% |
| N | 6.84% | 7.72% |

$^1$H-NMR (CDCl$_3$):
1.04 and 1.16 ppm (s) CH$_3$ (piperidine ring)
1.22–1.35 ppm (m) ax-CH$_2$ (piperidine ring)
1.69–1.72 ppm (m) eq-CH$_2$ (piperidine ring)
2.24 ppm (s) CH$_3$—N
2.65–2.75 ppm (m)

3.63–3.68 ppm (m) —O—CH$_2$—CH$_2$—O—
4.15 ppm (s) —O—CH$_2$—CO—
MALDI-MS: M$_n$=1171 M$_w$=1240

EXAMPLE 5

PEG-diacid-bis[di(3,3,5,5-tetramethylpiperidinyl) amide]

In a 1.5 liter sulfonation flask, equipped with KPG stirrer, internal thermometer and dripping funnel, 60 g (92 mmol) of the PEG-diacid dichloride prepared according to Example 4a) are dissolved in 400 ml of THF. This solution is cooled under argon to 0° C. A dripping funnel is charged with a solution consisting of 54 g (195 mmol) of bis(3,3,5,5-tetramethylpiperidinyl)-amine in 200 ml of THF. This solution is dripped slowly into the reaction flask, such that the temperature in the flask is ≦10° C. After the addition is complete, stirring is continued overnight at room temperature. The thick suspension is added to ice and 15 g of sodium hydroxide solution. The solution obtained is saturated with sodium chloride and is then extracted with 500 ml of chloroform. The organic phase is separated, dried with sodium sulfate and is then concentrated by evaporation. The residue is dried under high-vacuum.

This gives 81 g (35% of th.) of a viscous liquid.

| Microanalysis: | | |
|---|---|---|
| | calculated | found |
| C | 64.00% | 63.96% |
| H | 10.33% | 10.31% |
| N | 7.00% | 7.87% |

$^1$H-NMR (CDCl$_3$):
1.13 and 1.25 ppm (s) CH$_3$ (piperidine ring)
1.31–1.39 ppm (m) ax-CH$_2$ (piperidine ring)

1.63–1.70 ppm (m) eq-CH$_2$ (piperidine ring)
2.33–2.47 ppm (m)

3.63–3.72 ppm (m) —O—CH$_2$—CH$_2$—O—
4.17 ppm (s) —O—CH$_2$—CO—N—
MALDI-MS: M$_n$=1239 M$_w$=1407

EXAMPLE A1

Light-stabilisation of Polypropylene Fibres 2.5 g of the novel stabiliser of Example 1, together with 1 g of tris(2,4-di-tert-butylphenyl)-phophite, 1 g of calcium monoethyl-3,5-di-tert-butyl-4-hydroxybenzylphosphonate, 1 g of calcium stearate and 2.5 g of TiO$_2$ (Kronos RN 57), are mixed in a turbomixer with 1000 g of polypropylene powder (melt index 12 g/10 min, measured at 230° C./2.16 kg). The mixture is extruded at 200–230° C. to granules which are then processed to fibres using a pilot plant (Leonard; Sumirago/VA, Italy) under the following conditions:

extruder temperature: 190–230° C.
head temperature: 255–260° C.
draw ratio: 1:3.5
draw temperature: 100° C.
fibres: 10 den The fibres so prepared are exposed against a white background in a Weather-O-meter® type 65 WR (Atlas Corp.) at a black standard temperature of 63° C. according to ASTM D 2565-85. The residual tensile strength of the samples is determined after different exposure times. These values are used to calculate the exposure time T$_{50}$ after which the tensile strength of the samples is only half as high.

For comparison purposes, fibres are prepared without the novel stabilisers but under conditions which are otherwise the same.

The fibres stabilised according to this invention have excellent retention of strength.

EXAMPLE A2

Stabilisation of a Two-coat Lacquer

The novel stabiliser of Example 1 is incorporated into 5–10 g of xylene and is tested in a clear varnish of the following composition:

| | |
|---|---|
| Synthacryl ® SC 303[1] | 27.51 g |
| Synthacryl ® SC 370[2] | 23.34 g |
| Maprenal ® MF 650[3] | 27.29 g |
| butylacetate/butanol (37/8) | 4.33 g |
| isobutanol | 4.87 g |
| Solvesso ® 150[4] | 2.72 g |
| white spirit K-30[5] | 8.74 g |
| flow control agent Baysil ® MA[6] | 1.20 g |
| | 100.00 g |

[1] acrylate resin, of Hoechst AG; 65% solution in xylene/butanol 26:9
[2] acrylate resin, of Hoechst AG: 75% solution in Solvesso ® 100[4]
[3] melamine resin, of Hoechst AG; 55% solution in isobutanol
[4] producer: ESSO
[5] producer: Shell
[6] 1% in Solvesso ® 150; producer: Bayer AG 1% of the stabiliser of Example 1 (in xylene), based on the solids content of the varnish, are added to the clear varnish. A clear varnish not containing any light stabiliser serves as comparison.

The clear varnish is diluted with Solvesso® 100 to spray viscosity and is sprayed on a prepared aluminium sheet (coil coat, filler, silver metalic base coat) and is then stoved at 130° C. for 30 minutes, resulting in a dry film thickness of 40–50 μm of clear varnish.

The samples are then weathered in a UVCON® weathering apparatus of Atlas Corp. (UVB-313 lamps at a cycle of 4 h UV irradiation at 60° C. and 4 h condensation at 50° C.

The samples are examined at regular intervals for cracks.

The samples containing the novel stabiliser have high stability against cracking.

EXAMPLE A3

Stabilisation of a Photographic Material 0.087 g of the yellow coupler of formula

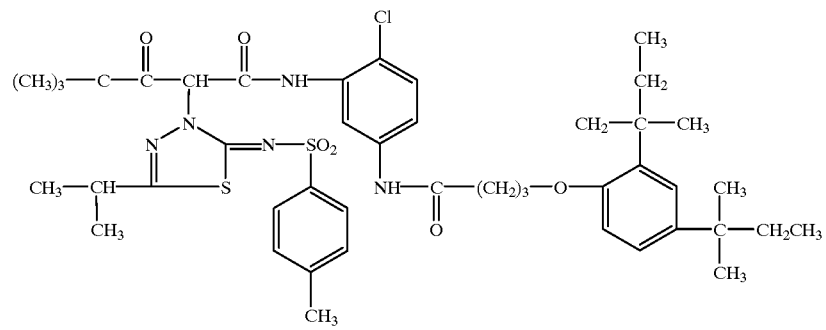

are dissolved in 2.0 ml of a solution of the novel stabiliser of Example 1 in ethyl acetate (2.25 g/100 ml). There are then added to 1.0 ml of this solution 9.0 ml of a 2.3% aqueous gelatine solution, adjusted to pH 6.5, and 1.744 g/l of the wetting agent of formula

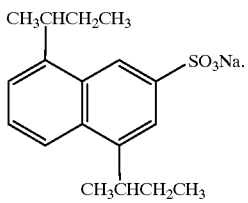

There are then added to 5.0 ml of the coupling emulsion so obtained 2 ml of a silver bromide emulsion having a silver content of 6.0 g/l and 1.0 ml of a 0.7% aqueous solution of the curing agent of formula

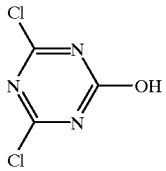

and this mixture is poured on a 13×18 cm paper which is coated with plastic material. After a curing time of 7 days, the samples are irradiated with 125 Lux·s behind a silver step wedge and are then processed by the Ektaprint 2® process, of Kodak.

The yellow wedges are irradiated in an Atlas Weather-O-meter® using a 2500 W-xenone lamp behind a UV filter (Kodak 2C) with a total of 60 kJoule/cm².

One sample is processed at the same time as standard without any stabiliser.

The loss in colour density which occurs during irradiation at the absorption maximum of the yellow colourant is determined using a Densitometer TR 924 A, of Macbeth.

The light stabilising effect can be determined from the loss of colour density. The smaller the loss in density, the higher the light stabilising effect.

The novel stabiliser has a good light stabilising effect.

EXAMPLE A4

Stabilisation of Polypropylene Tapes 1.0 g of the novel stabiliser of Example 1, together with 1 g of tris(2,4-di-tert-butylphenyl)-phosphite, 0.5 g of pentaerythritol-tetrakis(3-[3',5'-di-tert-butyl-4'-hydroxyphenyl]propionate) and 1 g of calcium stearate, is mixed in a turbomixer with 1000 g of polypropylene powder (STATOILMF; melt index 4.0 g/10 min, measured at 230° C./2.16 kg).

This mixture is extruded at 200–230° C. to granules which are then processed using a pilot plant (Leonard; Sumirago/VA, Italy) to 2.5 mm wide stretch tapes of 50 µm thickness under the following conditions:
 extruder temperature: 210–230° C.
 head temperature: 240–260° C.
 draw ratio: 1:6
 draw temperature: 110° C.

The tapes so obtained are exposed against a white background in a Weather-O-meter® type 65 WR (Atlas Corp.) at a black standard temperature of 63° C. according to ASTM D 2565-85. The residual tensile strength of the samples is measured after different exposure times. These values are used to calculate the exposure time $T_{50}$ after which the tensile strength of the samples is only half as high.

For comparison purposes, tapes are produced and tested which do not contain the novel stabiliser, under conditions which are otherwise the same.

The sample stabilised according to this invention has excellent retention of strength.

EXAMPLE A5

Stabilisation of Polyamide 6

100 Parts of unstabilised polyamide 6 granules (Ultramid®B3, of BASF) are powdered by cryogenic grinding and are charged with the novel stabiliser of Example 1. This mixture is mixed in a Henschel mixer for 2 minutes. The powder so obtained is dried at 80° C. for 6 hours and is then extruded in an extruder (type Berstorff) at a maximum of 240° C. and granulated. The granules so obtained are injection moulded in an injection moulding apparatus at a maximum of 240° C. to dumbbells 1.0 mm thick and to plates 2.0 mm thick.

The dumbbells are aged in a circulating air oven at 140° C. The progress of ageing is observed by determining the stress-strain-diagrams at intervals of 1–3 days. The end point is determined to be that time after which the residual strain has fallen to 50% of its initial value. The longer the time, the better the stabilisation.

The plates are aged in a circulating air oven at 80° C. for 1500 hours. The yellowness index (YI) of these plates is determined according to ASTM D 192570. Low YI values denote little discoloration, high YI values strong discoloration of the samples. The less discoloration, the more effective the stabiliser mixture.

For comparison purposes, samples are prepared and tested without the novel stabiliser, under conditions which are otherwise the same.

The novel stabiliser has a good light stabilising effect and the sample stabilised according to this invention has excellent retention of strength.

EXAMPLE A6

Stabilisation of Polyoxymethylene

Polyoxymethylene (Hostaform® C) is kneaded in a Brabender plasticorder with 0.3% by weight of calcium stearate, 0.3% by weight of a stabiliser of formula

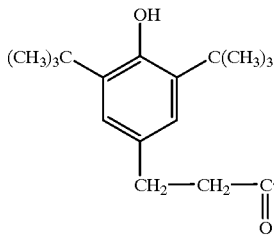 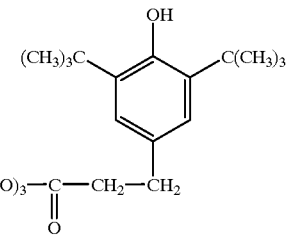

and 0.3% by weight of the novel UV absorber of Example 1 for 7 minutes at 190° C. and at 30 rpm.

The material is then moulded at 190° C. at a pressure of 3000 psi to plates 1 mm thick; the processing time in this step is 3 minutes.

The plates are exposed to irradation at 60° C. and at an atmospheric humidity of 23% using a UV-A source at a distance of 20 cm. The UV-A source consists of 5 TL/09 fluorescent lamps and 5 TL/12 lamps (wavelength range 295–400 nm). The yellowness index (YI, method ASTM D-1925) which passes a maximum a the UV irradiation of polyoxymethylene is determined at regular intervals. This maximum is caused by the first microcracks which cannot yet be visually observed. During further irradiation, cracks become visible in the plates at a later time.

For comparison purposes, samples are prepared and tested without any novel stabiliser, under conditions which are otherwise the same.

The novel stabiliser has a good light stabilising effect, i.e. the time (in weeks) to the YI maximum or to visible cracking is markedly longer than is the case without novel stabiliser.

What is claimed is:

1. A compound of formula 1

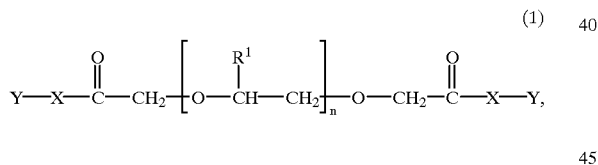 (1)

and a compound of formula 2

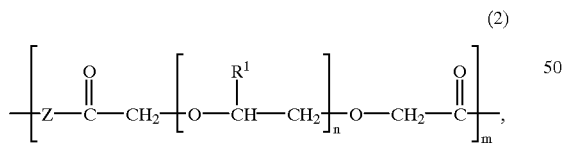 (2)

wherein $R^1$ is H or $CH_3$, and

Y is the group

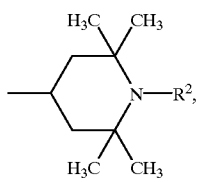

-continued

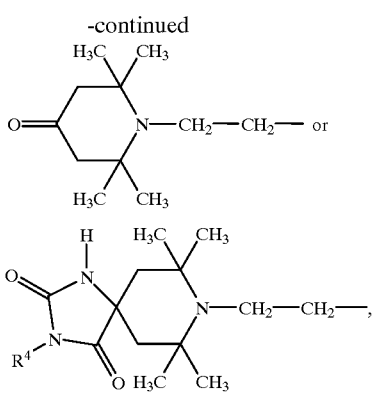

X is O or $NR^3$ $R^2$ is H, $C_1$–$C_{20}$alkyl, $C_1$–$C_{20}$hydroxyalkyl, O—$C_1$–$C_{20}$alkyl, CO—$C_1$–$C_{20}$alkyl, O—$C_5$–$C_8$cycloalkyl, $C_2$–$C_{20}$alkenyl, $C_2$–$C_{20}$alkynyl, $C_6$–$C_{20}$aryl, CO—$C_6$–$C_{20}$aryl, $C_7$–$C_{20}$aralkyl, CO—$C_7$–$C_{20}$aralkyl, and $R^3$ is H, $C_1$–$C_{20}$alkyl or

and $R^4$ is H, $C_1$–$C_{20}$alkyl, CO—$C_1$–$C_{20}$alkyl, CO—$C_6$–$C_{20}$alkyl, or CO—$C_7$–$C_{20}$aralkyl, and Z is

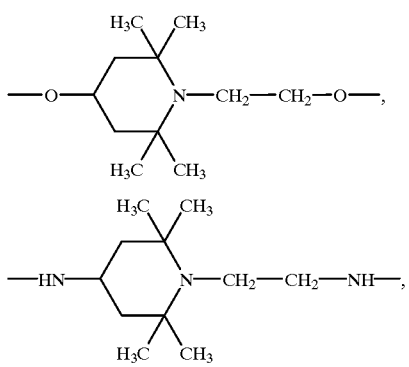

-continued

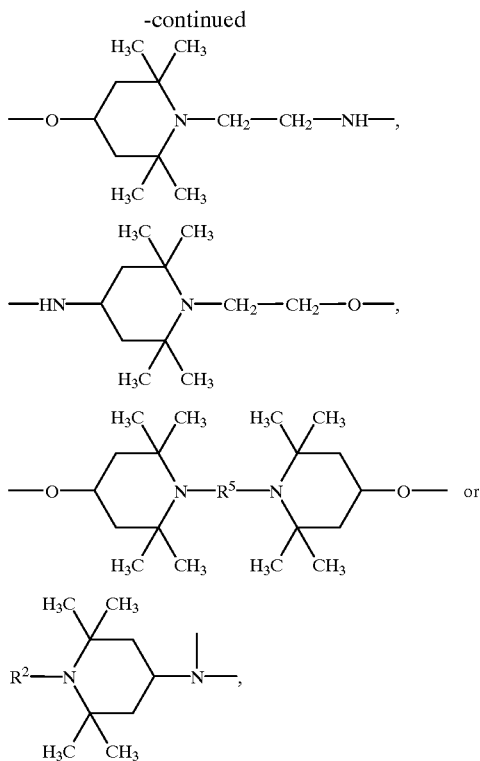

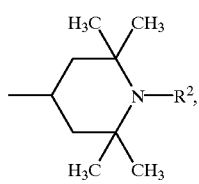

and $R^5$ is $C_1-C_{20}$alkylene, $C_2-C_{20}$alkenylene or $C_2-C_{20}$alkynylene, and n is a number from 1 to 100, and m is a number from 1 to 100.

2. A compound according to claim 1, wherein $R^2$ is H, $C_1-C_{12}$alkyl, $C_1-C_{12}$hydroxyalkyl, O—$C_1-C_{12}$alkyl, CO—$C_1-C_{12}$alkyl, O—$C_5-C_8$cycloalkyl, $C_2-C_{12}$alkenyl, $C_2-C_{12}$alkynyl, $C_6-C_{14}$aryl, CO—$C_6-C_{14}$aryl, $C_7-C_{15}$aralkyl or CO—$C_7-C_{15}$aralkyl.

3. A compound according to claim 1, wherein $R^2$ is H, $C_1-C_8$alkyl, O—$C_1-C_8$alkyl, O—$C_5-C_8$cycloalkyl, $C_2-C_8$alkenyl or $C_2-C_8$alkynyl.

4. A compound according to claim 1, wherein $R^3$ is H, $C_1-C_{12}$alkyl or

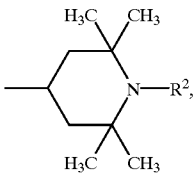

and $R^4$ is H, $C_1-C_{12}$alkyl, CO—$C_1-C_{12}$alkyl, CO—$C_6-C_{14}$aryl or CO—$C_7-C_{15}$aralkyl.

5. A compound according to claim 4, wherein $R^3$ is H or

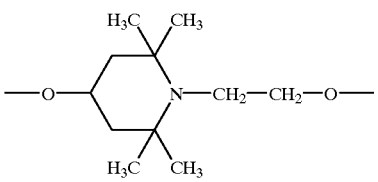

and $R^4$ is H, $C_1-C_8$alkyl, CO—$C_1-C_8$alkyl, CO-phenyl or CO-phenylalkyl.

6. A compound according to claim 1, wherein

Z is

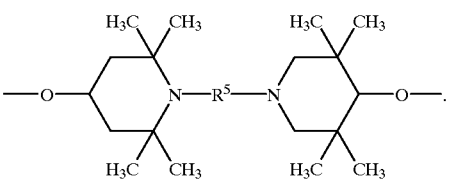

or

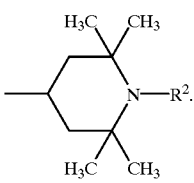

7. A compound according to claim 1, wherein n is a number from 1 to 50.

8. A compound according to claim 1, wherein m is a number from 1 to 50.

9. A compound of formula 1 according to claim 1.

10. A compound according to claim 9, wherein

Y is a group

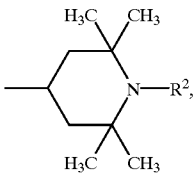

11. A compound according to claim 9, wherein

Y is a group

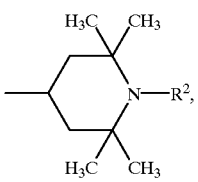

$R^2$ is H or $C_1-C_4$alkyl, $R^3$ is H or

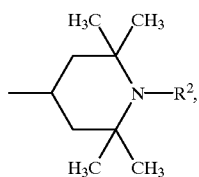

and n is a number from 5 to 25.

12. A composition, which comprises a) an organic material susceptible to oxidative, thermal or/and actinic degradation/build-up, and b) at least one novel compound according to claim 1 as stabiliser.

13. A composition according to claim 12, wherein component a) is an organic polymer.

14. A composition according to claim 12, wherein component a) is a synthetic polymer.

15. A composition according to claim 12, wherein component a) is a polar polymer or a surface coating resin based on acrylic, alkyd, polyurethane, polyester or polyamide resins or correspondingly modified resins.

16. A composition according to claim 12, which comprises further customary additives in addition to the components a) and b).

17. A composition according to claim 12, which comprises 0.01 to 10% by weight of component b), based on the weight of the composition.

18. A method of stabilising organic material against damage by light, oxygen and/or heat, which comprises admixing to this material a compound as claimed in claim 1.

* * * * *